(12) United States Patent
Steinbach et al.

(10) Patent No.: US 7,708,730 B2
(45) Date of Patent: May 4, 2010

(54) TEMPLATE SYSTEM FOR MULTI-RESERVOIR IMPLANTABLE PUMP

(75) Inventors: Bernd Steinbach, Friedberg (DE); Sidney David, Holmdel, NJ (US)

(73) Assignee: Palyon Medical (BVI) Limited, Tortola (VG)

( * ) Notice: Subject to any disclaimer, the term of this patent is extended or adjusted under 35 U.S.C. 154(b) by 425 days.

(21) Appl. No.: 11/342,391

(22) Filed: Jan. 30, 2006

(65) Prior Publication Data

US 2007/0185470 A1    Aug. 9, 2007

(51) Int. Cl.
*A61M 31/00* (2006.01)

(52) U.S. Cl. .................................... 604/500; 604/116

(58) Field of Classification Search ......... 604/115–117, 604/500, 502, 510, 890.1, 891.1, 892.1, 288.01–288.04; 128/DIG. 12, DIG. 13
See application file for complete search history.

(56) References Cited

U.S. PATENT DOCUMENTS

| | | | |
|---|---|---|---|
| 2,245,350 A * | 6/1941 | Marshall | 33/511 |
| 3,951,147 A | 4/1976 | Tucker et al. | |
| 4,003,379 A | 1/1977 | Ellinwood, Jr. | |
| 4,193,397 A | 3/1980 | Tucker et al. | |
| 4,258,711 A | 3/1981 | Tucker et al. | |
| 4,544,371 A | 10/1985 | Dormandy, Jr. et al. | |
| 4,548,607 A | 10/1985 | Harris | |
| 4,588,394 A | 5/1986 | Schulte et al. | |
| 4,634,427 A | 1/1987 | Hannula et al. | |
| 4,668,231 A | 5/1987 | de Vries et al. | |
| 4,699,615 A | 10/1987 | Fischell et al. | |
| 4,714,462 A | 12/1987 | DiDomenico | |
| 4,747,832 A | 5/1988 | Buffet et al. | |
| 4,813,951 A | 3/1989 | Cannon | |
| 4,828,551 A | 5/1989 | Gertler et al. | |
| 4,838,887 A | 6/1989 | Idriss | |
| 4,898,584 A | 2/1990 | Borsanyi et al. | |
| 4,908,019 A | 3/1990 | Urquhart et al. | |
| 4,969,873 A | 11/1990 | Steinbach et al. | |
| 5,011,477 A | 4/1991 | Winchell et al. | |

(Continued)

FOREIGN PATENT DOCUMENTS

DE      20311947 U1    11/2003

(Continued)

OTHER PUBLICATIONS

Udelsman et al., "Intraperitoneal delviery of insulin via mechanical pump:surgical implications", Mar. 3, 2000, Langenbeck's Arch Surg (2000) 385:367-372.*

(Continued)

*Primary Examiner*—Nicholas D Lucchesi
*Assistant Examiner*—Theodore J Stigell
(74) *Attorney, Agent, or Firm*—Lerner, David, Littenberg, Krumholz & Mentlik, LLP

(57) ABSTRACT

A template system for use in conjunction with a multiple reservoir or chambered implantable infusion pump is disclosed. The template system preferably includes at least one template having opening(s) for guiding a needle or syringe to various ports of the multiple reservoir pump. Preferably, each template includes at least two surfaces for cooperating with a like portions of the implantable pump, for properly seating the template on the pump. A kit is also disclosed including three templates for guiding injections into different ports of the pump.

13 Claims, 11 Drawing Sheets

U.S. PATENT DOCUMENTS

| | | | |
|---|---|---|---|
| 5,085,644 A | 2/1992 | Watson et al. | |
| 5,085,656 A | 2/1992 | Polaschegg | |
| 5,146,933 A * | 9/1992 | Boyd | 128/899 |
| 5,152,753 A | 10/1992 | Laguette et al. | |
| 5,167,633 A | 12/1992 | Mann et al. | |
| 5,205,820 A | 4/1993 | Kriesel | |
| 5,207,666 A | 5/1993 | Idriss et al. | |
| 5,236,689 A | 8/1993 | Wong et al. | |
| 5,242,406 A | 9/1993 | Gross et al. | |
| 5,304,153 A | 4/1994 | Tsujikawa | |
| 5,336,194 A | 8/1994 | Polaschegg et al. | |
| 5,667,504 A | 9/1997 | Baumann et al. | |
| 5,716,343 A | 2/1998 | Kriesel et al. | |
| 5,722,957 A | 3/1998 | Steinbach | |
| 5,758,667 A * | 6/1998 | Slettenmark | 128/899 |
| 5,766,150 A | 6/1998 | Langkau | |
| 5,769,823 A | 6/1998 | Otto et al. | |
| 5,776,103 A | 7/1998 | Kriesel et al. | |
| 5,785,688 A | 7/1998 | Joshi et al. | |
| 5,792,104 A | 8/1998 | Speckman et al. | |
| 5,814,019 A | 9/1998 | Steinbach et al. | |
| 5,836,915 A | 11/1998 | Steinbach et al. | |
| 5,840,063 A | 11/1998 | Flaherty | |
| 5,895,428 A | 4/1999 | Berry | |
| 5,906,597 A | 5/1999 | McPhee | |
| 5,976,109 A | 11/1999 | Heruth | |
| 6,086,555 A | 7/2000 | Eliasen et al. | |
| 6,179,806 B1 | 1/2001 | Sansoucy | |
| 6,280,416 B1 | 8/2001 | Van Antwerp et al. | |
| 6,283,944 B1 | 9/2001 | McMullen et al. | |
| 6,554,822 B1 | 4/2003 | Holschneider et al. | |
| 6,620,151 B2 | 9/2003 | Blischak et al. | |
| 6,673,091 B1 * | 1/2004 | Shaffer et al. | 606/201 |
| 6,730,060 B1 | 5/2004 | Steinbach et al. | |
| 6,764,472 B1 | 7/2004 | Burke et al. | |
| 6,796,956 B2 | 9/2004 | Hartlaub et al. | |
| 6,805,693 B2 | 10/2004 | Gray et al. | |
| 6,902,544 B2 | 6/2005 | Ludin et al. | |
| 6,932,114 B2 | 8/2005 | Sparks | |
| 7,044,932 B2 * | 5/2006 | Borchard et al. | 604/116 |
| 7,083,593 B2 | 8/2006 | Stultz | |
| 7,108,686 B2 | 9/2006 | Burke et al. | |
| 7,150,741 B2 | 12/2006 | Erickson et al. | |
| 7,214,221 B2 | 5/2007 | Fentress et al. | |
| 7,367,968 B2 | 5/2008 | Rosenberg et al. | |
| 2002/0151875 A1 | 10/2002 | Haller | |
| 2002/0156361 A1 | 10/2002 | Popowski et al. | |
| 2002/0156462 A1 | 10/2002 | Stultz | |
| 2003/0175149 A1 | 9/2003 | Searles et al. | |
| 2003/0199813 A1 | 10/2003 | Struble | |
| 2004/0078000 A1 * | 4/2004 | Borchard et al. | 604/116 |
| 2004/0143242 A1 | 7/2004 | Ludin et al. | |
| 2005/0070875 A1 | 3/2005 | Kulessa | |
| 2005/0113745 A1 | 5/2005 | Stultz | |
| 2005/0273082 A1 | 12/2005 | Olsen | |
| 2006/0089619 A1 | 4/2006 | Ginggen | |
| 2006/0271021 A1 | 11/2006 | Steinbach | |
| 2006/0271022 A1 | 11/2006 | Steinbach et al. | |

FOREIGN PATENT DOCUMENTS

| | | |
|---|---|---|
| WO | 03/068049 | 8/2003 |
| WO | 2005007223 | 1/2005 |
| WO | 2005044343 | 5/2005 |
| WO | 2005079885 | 9/2005 |

OTHER PUBLICATIONS

Karas, Beverly Schambura, "Refilling an implanatable pump", Nov. 1995.*

Institute For Safe Medication Practices, "Template for Disaster? Fatal Injection into Wrong Port of Implanted Infusion Pump", Jan. 15, 2004.*

Medtronic Educational Brief, Pump Refill Techniques:IsoMed Pump Systems, Aug. 2003.*

International Search Report, PCT/US07/01828.

International Search Report, PCT/US06/20135.

Supplementary Partial European Search Report, EP 07716956, mailed May 8, 2009.

* cited by examiner

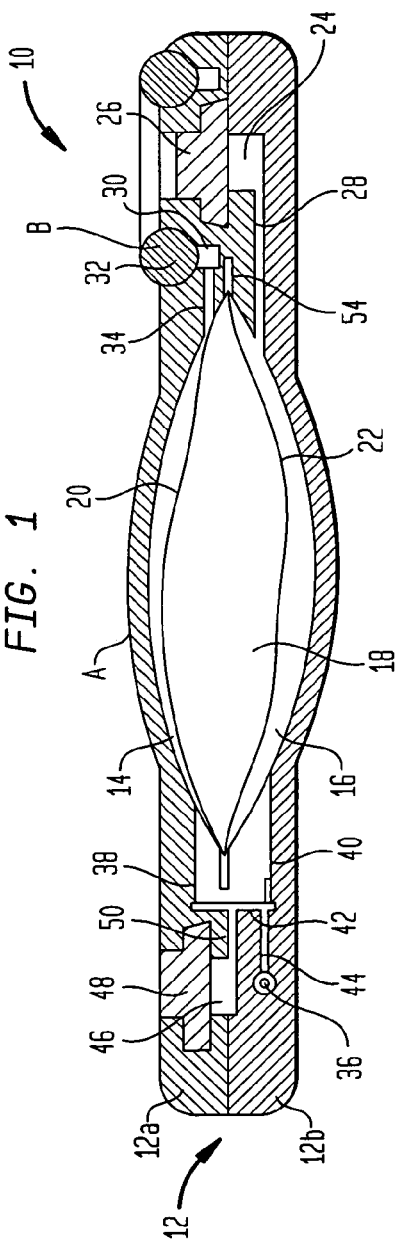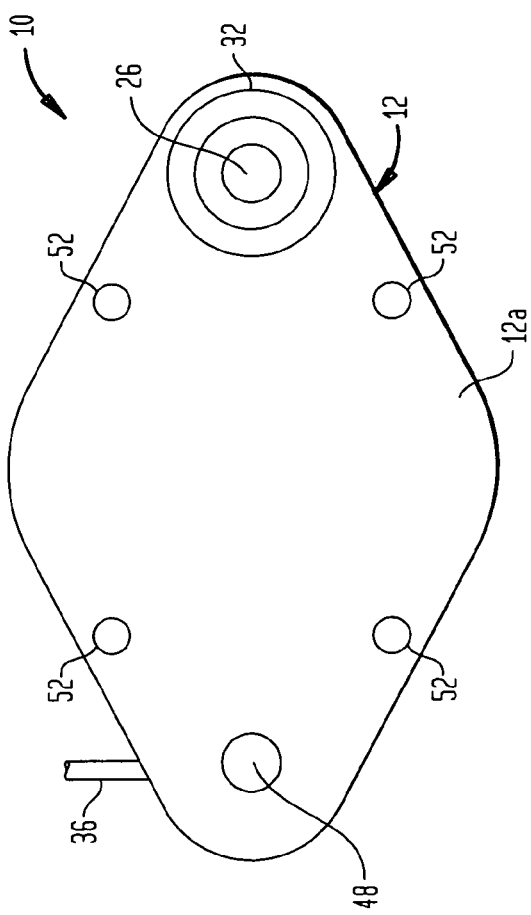

TEMPLATE SYSTEM FOR MULTI-RESERVOIR IMPLANTABLE PUMP

BACKGROUND OF THE INVENTION

The present invention relates to implantable devices, and more particularly to a template system for use in conjunction with a multi-reservoir implantable pump.

Implantable pumps have been well known and widely utilized for many years. Typically, pumps of this type are implanted into patients who require the delivery of active substances or medication fluids to specific areas of their body. For example, patients that are experiencing severe pain may require painkillers daily or multiple times per day. Absent the use of an implantable pump or the like, a patient of this type would be subjected to one or more painful injections of such medication fluids. In the case of pain associated with more remote areas of the body, such as the spine, these injections may be painful for the patient. Furthermore, attempting to treat conditions such as this through oral or intravascular administration of medication often requires higher doses of medication and may cause severe side effects. Therefore, it is widely recognized that utilizing an implantable pump may be beneficial to both a patient and the treating physician.

Many implantable pump designs have been proposed. For example, U.S. Pat. No. 4,969,873 ("the '873 patent"), the disclosure of which is hereby incorporated by reference herein, teaches one such design. The '873 is an example of a constant flow pump, which typically include a housing having two chambers, a first chamber for holding the specific medication fluid to be administered and a second chamber for holding a propellant. A flexible membrane may separate the two chambers such that expansion of the propellant in the second chamber pushes the medication fluid out of the first chamber. This type of pump also typically includes an outlet opening connected to a catheter for directing the medication fluid to the desired area of the body, a replenishment opening for allowing for refilling of medication fluid into the first chamber and a bolus opening for allowing the direct introduction of a substance through the catheter without introduction into the first chamber. Both the replenishment opening and the bolus opening are typically covered by a septum that allows a needle or similar device to be passed through it, but properly seals the openings upon removal of the needle. As pumps of this type provide a constant flow of medication fluid to the specific area of the body, they must be refilled periodically with a proper concentration of medication fluid suited for extended release.

Thus, although these implantable devices dramatically decrease the amount of injections a patient is required to receive in order to treat a specific problem, a small number of injections are still required to regularly refill the implantable pump. These refilling injections are often difficult for a physician or other medical professional to administer, even though implantable pumps typically sit at or near the surface of a patient's skin, because of the lack of direct visibility of the pump and its openings. Furthermore, with each implantable pump generally including at least two different openings for admission of a needle therein, safety becomes a concern during refilling procedures. More particularly, it is vital that a long term supply of medication not be inadvertently directly injected into the patient through the aforementioned bolus port. Given the fact that the landscape of implantable pumps is changing to include more complicated multiple reservoir pumps, these safety concerns are often further exacerbated.

Therefore, there exists a need for a template system which decreases the difficulties and improves the safety of refilling procedures, especially during the refilling of multiple reservoir pumps or the like.

SUMMARY OF THE INVENTION

A first aspect of the present invention is a kit for use in refilling an implantable infusion pump having multiple ports. In accordance with one embodiment of this first aspect, the kit preferably includes at least three different templates. Each of the templates may include at least one opening therethrough, such that each of the templates allows the injection of fluid into a different port of the implantable infusion pump. The kit most preferably includes three templates. Each of the templates may also include at least two surfaces corresponding to portions of said implantable infusion pump. The at least two surfaces and portions preferably allow for proper alignment of the template with respect to the implantable pump. In other embodiments, the templates may also include at least two protrusions corresponding to depressions of the implantable infusion pump. Once again, the at least two protrusions preferably allow for proper alignment of the template with respect to the implantable pump. Finally, the templates may also includes at least one protrusion corresponding to at least one depression of the implantable infusion pump, and at least one surface corresponding to at least one portion of the implantable infusion pump.

A second aspect of the present invention is a template for use in refilling a multiple chamber implantable infusion pump. The template preferably includes a body having at least three openings therethrough. The template preferably allows the injection of fluid into at least a first and second chamber and direct injection into the bolus port. The template may also include at least two surfaces corresponding to portions of the implantable infusion pump. Alternatively, the template may include at least two protrusions corresponding to depressions of the implantable infusion pump. Finally, the template may include at least one protrusion corresponding to at least one depression of the implantable infusion pump, and at least one surface corresponding to at least one portion of the implantable infusion pump.

A third aspect of the present invention is a method of refilling an implantable pump which has been implanted in a patient. The method preferably includes the steps of placing a first template over a section of skin of the patient adjacent the pump, so as to align means on the first template with means on the implantable infusion pump, and injecting a needle through an opening formed in the first template, through the skin of the patient, and into a first port corresponding to a first chamber of the pump. The method further includes the steps of placing a second template over a section of skin of the patient adjacent the pump, so as to align means on the second template with means on the implantable infusion pump, and injecting a needle through an opening formed in the second template, through the skin of the patient, and into a second port corresponding to a second chamber of the pump. The method may also include the steps of placing a third template over a section of skin of the patient, so as to align means on the third template with means on the implantable infusion pump, and injecting a needle through an opening formed in the third template, through the skin of the patient, and into a third port of the pump, the third port allowing for direct injection into the patient.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 1 is a cross sectional front view of an implantable pump in accordance with an embodiment of the present invention.

FIG. 2 is a top view of the implantable pump shown in FIG. 1.

FIG. 3b is a top view of the template shown in FIG. 3a.

FIG. 4b is a top view of the template shown in FIG. 4a.

FIG. 5b is a top view of the template shown in FIG. 5a.

FIG. 7b is a side view of the multiple reservoir implantable pump shown in FIG. 7a.

DETAILED DESCRIPTION

Figure 3A:
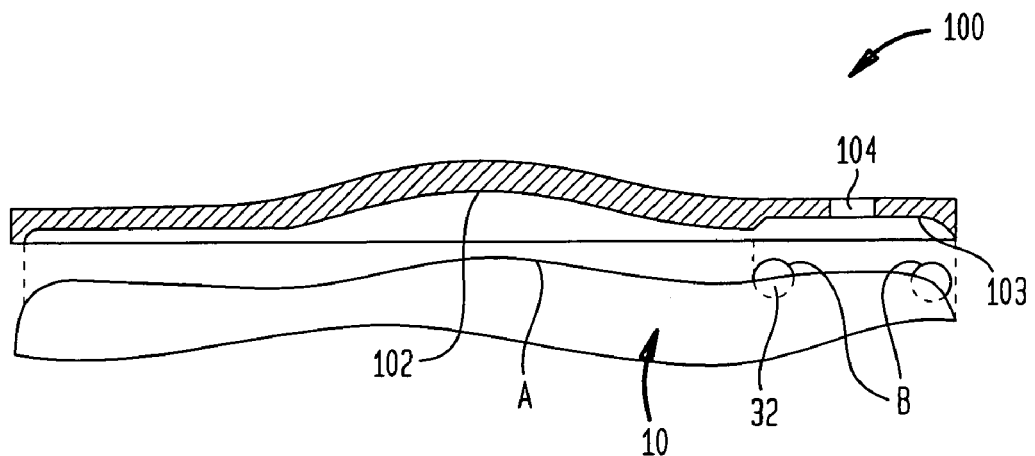
FIG. 3a is a cross sectional side view of a template for use in refilling one reservoir of the multiple reservoir pump of FIGS. 1 and 2, with a top surface of the pump being illustrated for purposes of clarity.
Figure 3B:
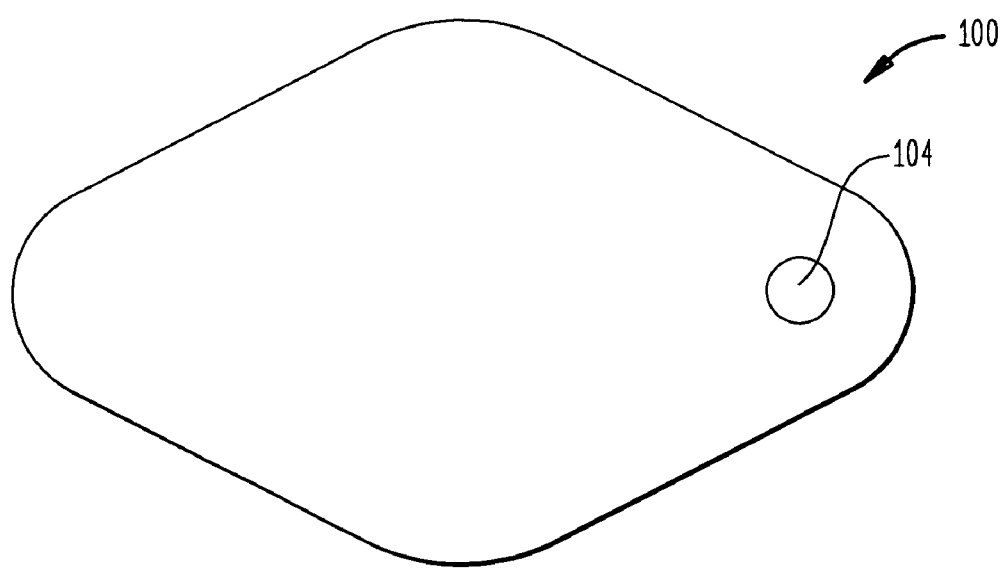
Figure 4A:
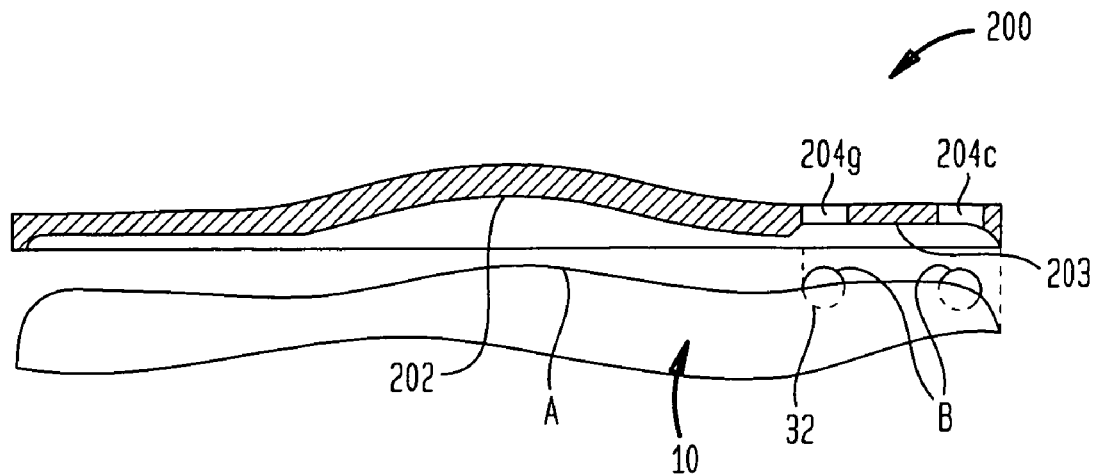
FIG. 4a is a cross sectional side view of another templates for use in refilling another reservoir of the multiple reservoir pump of FIGS. 1 and 2, with a top surface of the pump being illustrated for purposes of clarity.
Figure 4B:
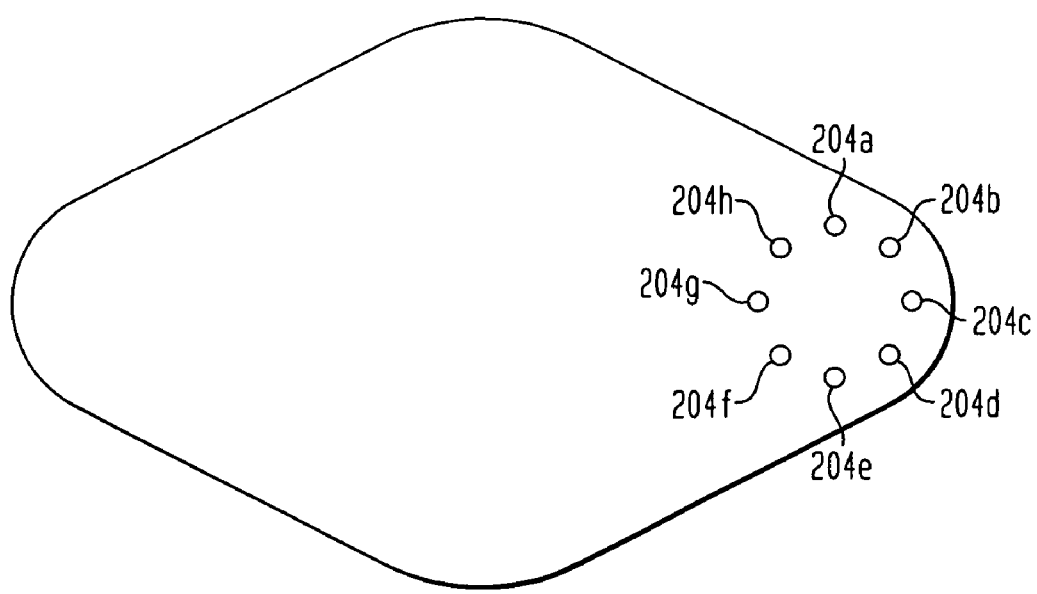
Figure 5A:
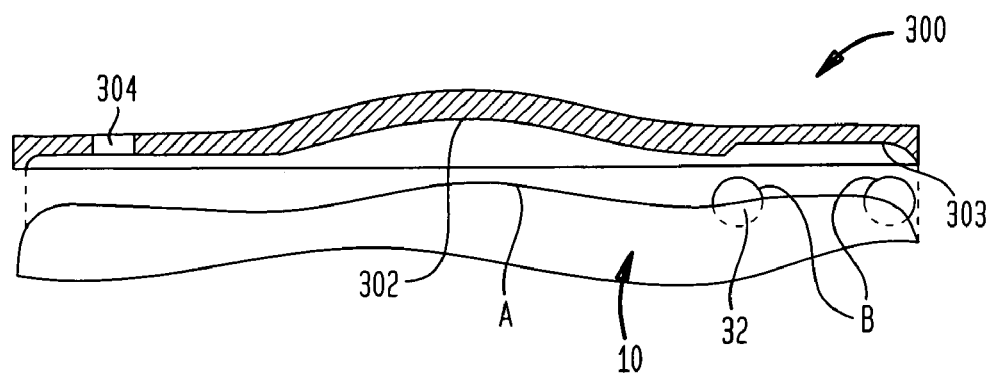
FIG. 5a is a cross sectional side view of yet another template for use in providing a bolus injection to a patient through the multiple reservoir pump of FIGS. 1 and 2, with a top surface of the pump being illustrated for purposes of clarity.
Figure 5B:
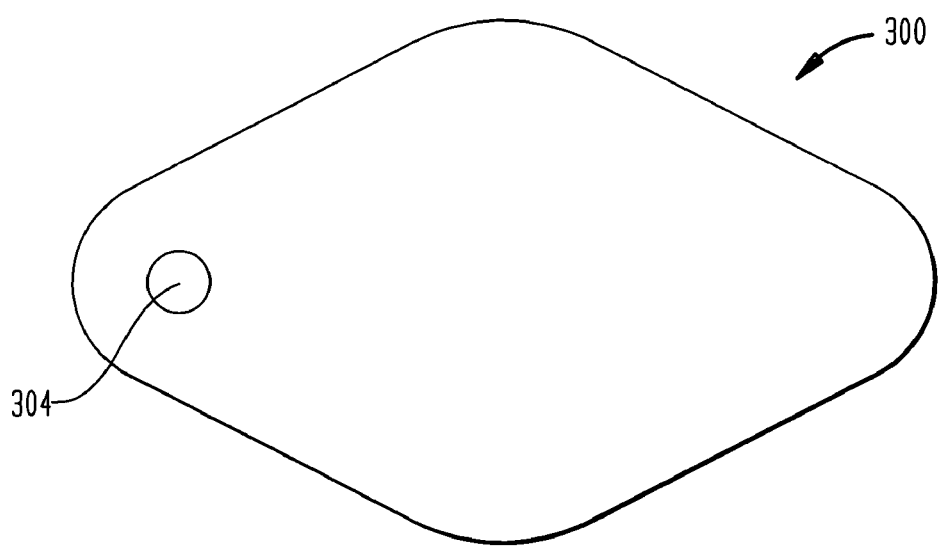

Examples of multiple reservoir pumps, as briefly discussed above, are taught in U.S. patent application Ser. Nos. 11/137, 284 and 11/136,771, which were concurrently filed on May 25, 2005, the disclosures of which are hereby incorporated by reference herein. FIGS. 1 and 2 of those applications are included herein as like FIGS. 1 and 2. Essentially, a multi-reservoir pump 10 is taught, having a housing 12 that defines chambers or reservoirs 14, 16, and 18. Chamber 18 is preferably formed between two flexible membranes 20 and 22, while chamber 14 is formed between a top portion 12a of housing 12 and membrane 20, and chamber 16 is formed between a bottom portion 12b of housing 12 and membrane 22. In preferred embodiments, chambers 14 and 16 are designed and configured to receive and house active substances such as medication fluids for the relief of pain, treatment of spasticity and neuro-mechanical deficiencies and the administration of chemotherapy, while chamber 18 is preferably designed and configured to contain a propellant which expands isobarically under the influence of body heat. This expansion necessarily displaces membranes 20 and 22, towards top portion 12a and bottom portion 12b respectively, so as to expel any active substances contained within chambers 14 and 16.

In the embodiment depicted in FIGS. 1 and 2, pump 10 further includes a first replenishment port 24 formed in both top portion 12a and bottom portion 12b. This port is preferably covered by a septum 26, which is capable of being pierced by an injection needle and, upon removal of such needle, is capable of automatically resealing itself. As pump 10 is designed to medicate a patient over a limited period of time, first replenishment port 24 is utilized for replenishing chamber 16 when empty or near empty. In addition, housing 12 preferably includes a second replenishment port 30 for replenishing chamber 14 with an active substance or the like. This port is also preferably covered by a second septum 32. However, as shown in FIGS. 1 and 2, port 30 and septum 32 are ring shaped, so that they extend around port 24. This design allows for both replenishment ports to be located in a relatively small area without requiring the need for a larger housing 12.

During a replenishment procedure, a physician and/or other medical professional typically inserts an injection needle into an area of a patient's body where pump 10 is located, such that it may pierce one of first septum 26 or second septum 32. Thereafter, operation of the needle causes injection of solution from the needle to pass into either chamber 14 through a passage 34 or chamber 16 through a passage 28. It is noted that the particular dimension of pump 10 and/or the patient's need may require such a process to be repeated at given intervals, for example, monthly, weekly, etc. In addition, as will be more fully discussed below, the replenishment process may be performed so as to vary the particular flow rate of a medication fluid to the patient. Pump 10, as shown in FIG. 1, also includes an outlet catheter 36 for remote delivery of a fluid contained within chambers 14 or 16 to a specific location within the body of a patient. Catheter 36 may be any well known catheter suitable for directing a medication fluid or the like to a location away from pump 10. For example, catheter 36 may direct medication fluid from a pump implanted at or near the surface of a patient's body to the spinal or other remote area. In the embodiment shown in FIG. 1, catheter 36 is in fluid communication with both chambers 14 and 16 through a series of connected passages. Specifically a first flow resistor 38 is connected to chamber 14, while a second flow resistor 40 is connected to chamber 16. It is noted that both resistors 38 and 40 may be any fluid resistor known in the art. In their most simplistic form, resistors 38 and 40 are essentially narrow tubes or capillaries which are dimensioned so as to allow a maximum flow rate therethrough. Thus, regardless of the flow rate of fluid from either chamber 14 or 16, resistors 38 and 40 act as restrictors and govern the maximum rate. Resistors 38 and 40 are preferably connected to a collecting duct 42, which is in turn connected to a tube or capillary 44 in communication with catheter 36.

In operation, expansion of propellant housed within chamber 18 exerts a force upon membranes 20 and 22. This force displaces membranes 20 and 22, towards top portion 12a and bottom portion 12b respectively, which in turn necessarily expels fluid contained in chambers 14 and 16 through resistors 38 and 40 respectively and ultimately out catheter 36. The flow rate which was determined by resistors 38 and 40 determines the flow rate of the fluid through and out of catheter 36.

In addition to the aforementioned first and second replenishment ports 24 and 30, pump 10 also preferably includes a bolus port 46 covered by a bolus septum 48. Essentially, this bolus port allows for direct introduction of a solution into outlet catheter 36 and to the specific target area of the body. This port is particularly useful when a patient requires additional or stronger medication, such as a single bolus injection, and/or when it is desired to test the flow path of catheter 36. Such an injection is performed in a similar fashion to the above discussed injection in replenishment ports 24 and 30. As shown in FIG. 1, fluid injected into bolus port 46 passes through bolus passage 50 and into collecting duct 42. Thereafter, similar to above, such fluid passes through tube 44 and out catheter 36. Thus, an injection into bolus port 46 bypasses resistors 38 and 40, and provides direct access to catheter 36, without any reduction in flow rate. It is also possible to utilize bolus port 46 to withdraw fluid from the body. For example, where pump 10 is situated within the body such that catheter 36 extends to the vertebral portion of the spinal column, a needle with a syringe connected thereto may be inserted into bolus port 46 and operated to pull spinal fluid through catheter 36 and into the syringe.

The design of pump 10 preferably allows for the selective administration of any fluid housed therein, at up to three different flow rates. As discussed above, upon the expansion of a propellant housed within chamber 18, any fluid housed within chambers 14 and 16 is ultimately expelled through catheter 36. The aforementioned resistors 38 and 40 dictate the maximum flow rate for any fluid being expelled from chambers 14 and 16 respectively. In certain preferred embodiments, these resistors differ in the maximum flow rate for which they allow. Thus, depending upon which chamber(s) is filled/injected with fluid, the flow rate through catheter 36 will preferably vary. For example, if chamber 14 is filled with a fluid, and chamber 16 is empty, the overall flow rate of fluid from pump 10 is determined by resistor 38. Alternatively, if chamber 16 is filled with a fluid, and chamber 14 is empty, the overall flow rate of fluid from pump 10 is determined by resistor 40. If both chambers 14 and 16 are filled with a fluid, the highest flow rate occurs and is determined by the combination of the flow rates dictated by resistors 38 and 40. Clearly, this three flow rate capability is beneficial in varying the flow rate of a medication fluid or the like depending upon the particular needs of a patient.

A doctor and/or other medical professional may easily utilize pump 10 so as to provide three different flow rates of medication to a patient. Initially, pump 10 may be implanted into the body of a patient by well known methods for implanting such implantable devices. As shown in FIG. 2, suture holes 52 may be useful in attaching pump 10 to a specific portion of the body so that catheter may be directed to the portion which requires the medication fluid or the like. Once pump 10 is implanted in the body of a patient, the aforementioned medical professional may essentially pick and choose which chambers to fill. As set forth above, filling of either chamber 14 or chamber 16 may provide either a first or second flow rate of fluid, while filling both may provide a third flow rate. Depending upon the particular conditions of the patient (e.g.—the patient's current level of pain), the medical professional may determine what chambers to fill and/or leave empty. In combination with the aforementioned direct bolus injection capability, this three flow design is clearly beneficial to both a patient and medical professional. As pump 10 is designed to house a limited amount of medication fluid, it must be refilled regularly. A doctor or nurse may utilize the regularly scheduled replenishment procedure as an opportunity to further monitor the patient and determine the proper flow rate for treating the patient's infirmity. Thus, if a doctor determines that the patient requires more medication fluid to be directed to the afflicted area, he/she may simply fill both chambers or the single chamber associated with the faster flow rate resistor. Alternatively, when less medication is desired, only one chamber or the chamber associated with the slower resistor may be filled.

In addition to the varying flow rate discussed above, the design of pump 10 also allows for the administration of up to two different active substances, or a combination of both, from a single pump. Clearly, the dual reservoir design of pump 10 as shown in FIGS. 1 and 2 may allow for two different medication fluids or the like to be housed in chambers 14 and 16. Thereafter, upon the expansion of a propellant housed within chamber 18, either one or both (depending on which chambers have been filled) may be administered to a patient.

Clearly, refilling of either of the ports of the above discussed pump 10, as well as direct injection into bolus port 46, is a required, but difficult procedure. In fact, as mentioned above, it is one that must be done with great care, as mistakes could pose serious health risks for the patient. As shown in FIGS. 3a-5b, in accordance with the present invention, a template system is provided for guiding needles/syringes into the above described implantable pump 10. The template system preferably includes a first template 100 (depicted in FIGS. 3a and 3b), a second template 200 (depicted in FIGS. 4a and 4b) and a third template 300 (depicted in FIGS. 5a and 5b). Each of these templates, as well as their preferred use will be discussed further below. It is important to note that each of the templates are useful in guiding needles/syringes into an implantable pump 10 or the like, and also in self-aligning itself so that injection into the correct desired port is not only achieved, but guaranteed.

First template 100 is to be utilized in refilling chamber 16 with a medication fluid or the like. As discussed above, a doctor or other medical professional will typically use a syringe/needle to pierce septum 26 and inject fluid contained therein into chamber 16. Heretofore, as implantable pump 10 is preferably implanted close to the surface of the skin of a patient, this procedure has often been performed by feeling the surface of the pump and gauging the correct positioning of septum 26 and first replenishment port 24. However, this type of guessing lends itself to causing many improper injections. First template 100 is designed so as to circumvent these problems, by providing a contoured seating surface 102, a recessed seating surface 103 and a first guide opening 104. Contoured seating surface 102 is preferably concave in shape and adapted to cooperate with a corresponding convex portion A of the top surface of pump 10. Recessed seating surface 103 is also preferably shaped so as to cooperate with a corresponding extending portion B of the top surface of pump 10, defined, in the case of the pump of FIG. 1, by the uppermost extremities of the ring-like septum 32. These two surfaces of template 100 thus cooperate with pump 10 so that engagement of the two surfaces necessarily aligns guide opening 104 with port 24 and septum 26. There is simply no other way for template 100 to properly overlie pump 10, unless the corresponding surfaces of the two components engage one another. It is noted that opening 104 is preferably similarly sized and configured with respect to septum 26. Thus, in a refilling procedure, a doctor/medical professional will place template 100 over the skin of a patient (not shown) in the area of pump 10 with concave surface 102 receiving pump surface A. The template will then be rotated about contoured seating surface 102 until recessed seating surface 103 seats on surfaces B of pump 10. Thereafter, the doctor/medical professional can be assured that injection in the area of opening 104 will necessarily cause medication fluid or the like to refill chamber 16.

As shown in FIGS. 4a-5b, templates 200 and 300 are similar in nature to template 100. Both second template 200 and third template 300 include contoured seating surfaces (surfaces 202 and 302 respectively) and recessed seating surfaces (surfaces 203 and 303 respectively), but with different openings associated with different ports of pump 10. More particularly, template 200 includes a plurality of openings 204a-204h, which correspond to different positions around second replenishment port 30 and second septum 32. Thus, placement of second template 200 over pump 10, so as to engage concave seating surface 202 with convex portion A of the top surface of pump 10 and recessed seating surface 203 with extending portion B of pump 10, will guarantee that a syringe or needle inserted through any of openings 204a-204h will inject fluid into chamber 14. Similarly, template 300 includes opening 304 for guiding a syringe or needle through bolus septum 48 and into bolus port 46. Thus, when a direct injection is desired, a doctor or other medical professional can be assured that he or she is properly injecting the fluid into bolus port 46. Similarly, should a withdrawal of spinal fluid or the like be desired through bolus port 46, third template 300 ensures that a needle is properly placed. Once again, surfaces 302 and 303 cooperate with portions A and B of pump 10 to ensure proper seating and alignment of template 300.

In addition to having like contoured surfaces for cooperating with the top surface of pump 10, templates 100, 200 and 300 are preferably constructed of like materials. For example, in certain embodiments, the templates are constructed of polymeric materials, such as polycarbonate, polypropylene, polyethylene and polyselphone. In a certain preferred embodiment, polycarbonate is utilized. However, it is noted that each of the templates can be constructed of many different materials, including but not limited to metals or other rigid materials. Typically, it is desired to have the templates constructed so as to be relatively stiff, to ensure consistent cooperation with pump 10. Nevertheless, it is contemplated to provide a template with a flexible construction, where the construction may provide a more comfortable cooperation for the patient, such as patients who are overly obese.

It is also envisioned to provide a template with a recessed surface shaped differently than recessed surfaces 103, 203 and 303 for cooperating with a correspondingly shaped raised portion of pump 10. Any cooperating shape is clearly within the scope of the invention. In addition, although not shown in the drawings, it is also envisioned to provide a template with a seating surface in the form of a downward protrusion, (rather than a recessed surface) which cooperates with a depression in the surface of the pump. It is also noted that while the templates shown in FIG. 3a-5b are all sized and shaped alike, and with that of pump 10, it is possible to size and shape each of the templates differently with respect to each other and pump 10. As long as the templates, and corresponding pumps, include structure for ensuring the proper alignment of the templates with pump 10, such that their respective openings properly align with the desired ports of the pump, any shape may be utilized.

Figure 6:
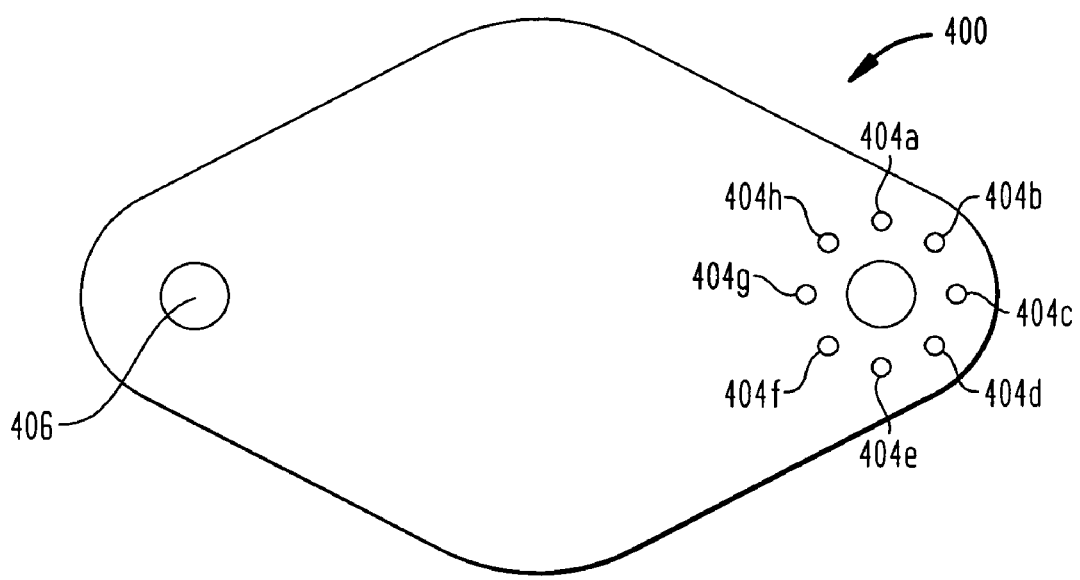
FIG. 6 is a top view of a template for use in refilling two reservoirs of the multiple reservoir pump of FIGS. 1 and 2, and for use in providing a bolus injection to a patient through the same pump.

It is noted that the use of templates 100, 200 and 300 ensures that a doctor or other medical professional cannot inadvertently inject a medicament or other fluid into an incorrect port of pump 10. Rather, providing the three separate templates requires the medical professional to consciously choose the correct template for the particular port to be injected. Thereafter, the particular template is seated and thereby properly aligned with the pump so that a syringe or needle may only access the particular port desired to be injected. Templates 100, 200 and 300 may include indicia printed thereon to clearly identify which ports the templates correspond to. However, it is also possible to provide a single template 400 (depicted in FIG. 6) for use in injecting fluid into the various ports of pump 10. As shown in FIG. 6, template 400 includes an opening 402 for directing a needle or syringe to refill chamber 16, a plurality of openings 404a-404h for use in refilling chamber 14, and an opening 406 for use in providing a direct injection to a patient via bolus port 46. Template 400 also preferably includes concave and recessed seating surfaces (not shown) similar to those discussed above, for cooperating with pump 10. In use, template 400 is simply seated over pump 10 so as to engage its contoured seating surface with convex portion A of the top surface of pump 10 and its recessed seating surface with extending portion B of the top surface of pump 10. As a result, all openings will necessarily align over the proper septum. Thereafter, the doctor or medical professional may simply insert a needle or the like through the opening corresponding to the port they wish to fill. Template 400 may include indicia or other identifiers for indicating which port the particular opening relates to.

Figure 7A:
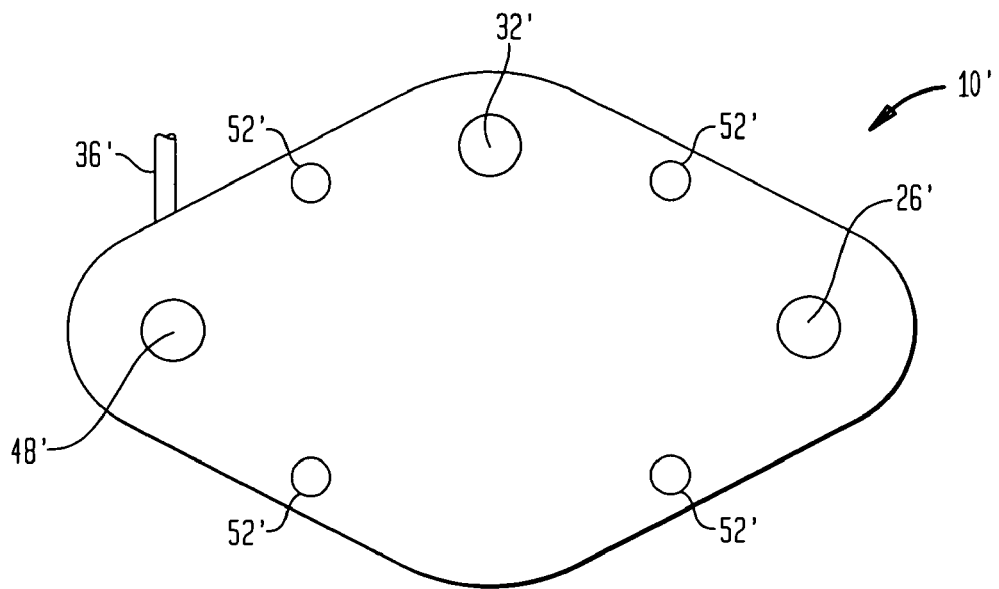
FIG. 7a is a top view of another embodiment multiple reservoir implantable pump.

A second embodiment implantable pump and corresponding template system is depicted in FIGS. 7a-10. As shown in FIGS. 7a-7b, a pump 10' includes a different configuration than that of pump 10, with like elements being identified with like reference numerals and a prime ("'") identifier. Essentially, pump 10' is identical to aforementioned pump 10, except for port 30' and septum 32' being repositioned away from port 24' and septum 26'. Thus, pump 10' includes three different spaced apart ports 24', 30' and 46' (not shown). However, operation of pump 10', as well as its different components, remains substantially similar to pump 10, as discussed above.

Figure 7B:
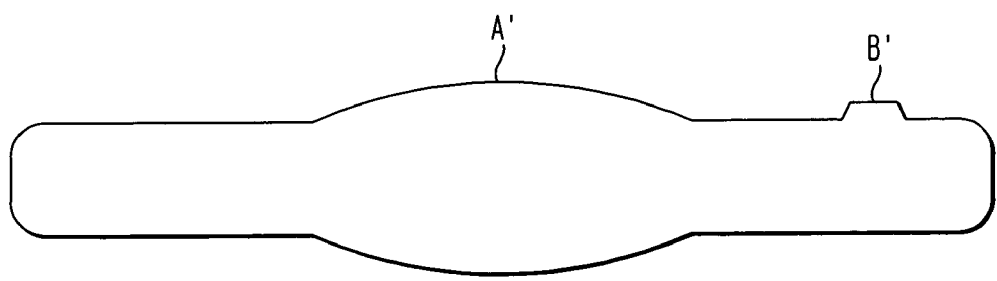
Figure 8:
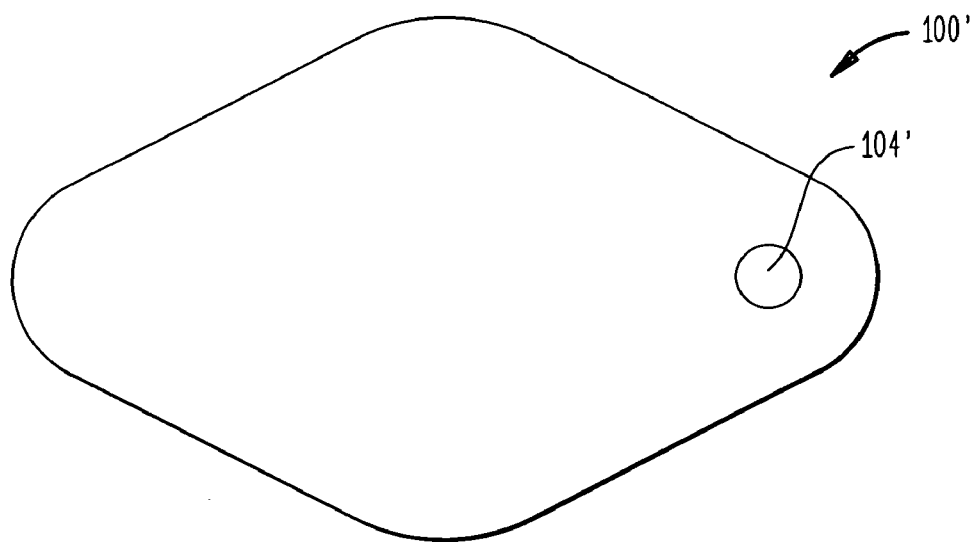
FIG. 8 is a top view of a template for use in refilling one reservoir of the multiple reservoir pump of FIG. 7.
Figure 9:
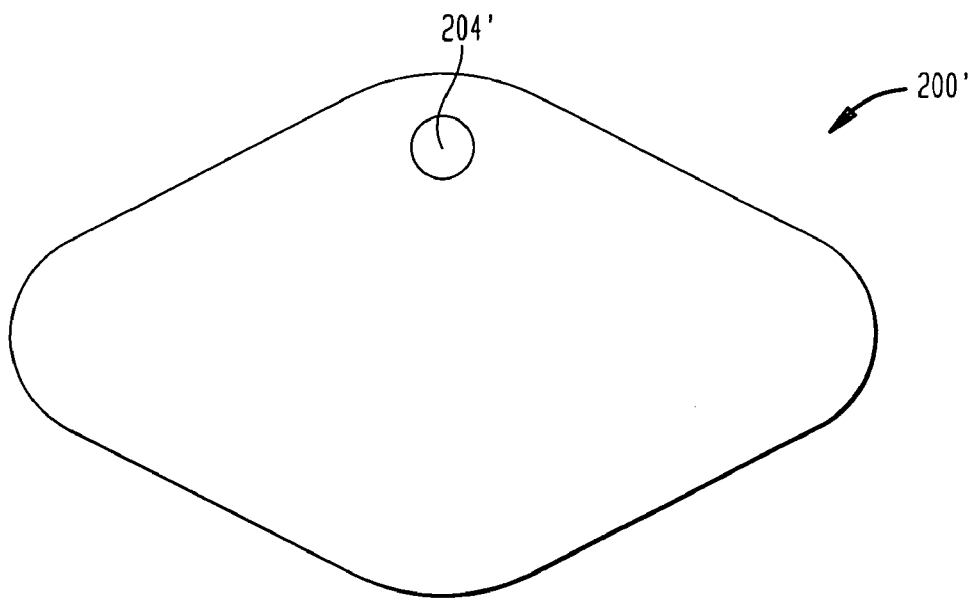
FIG. 9 is a top view of a template for use in refilling another reservoir of the multiple reservoir pump of FIG. 7.
Figure 10:
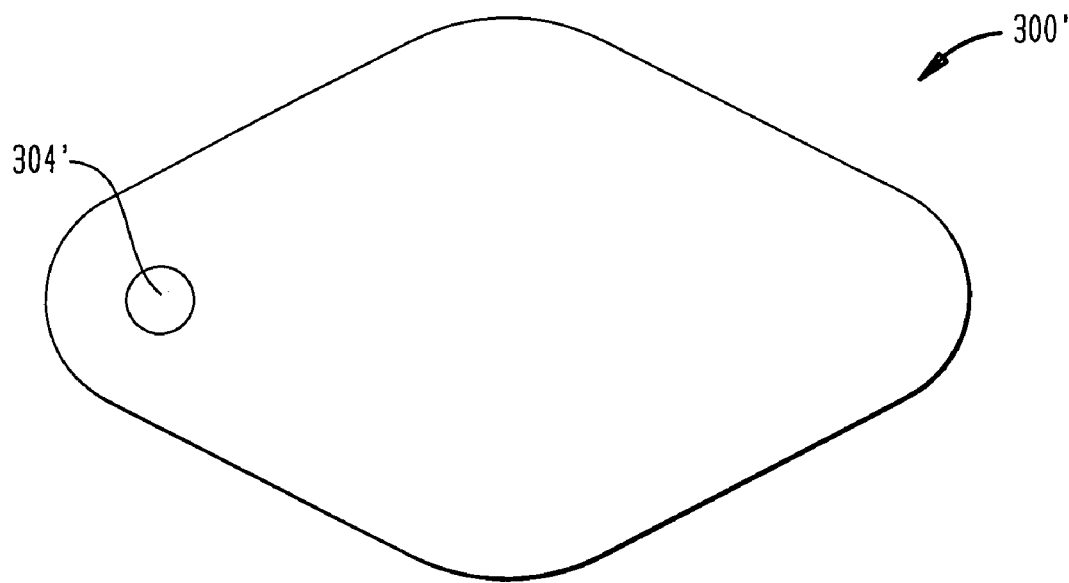
FIG. 10 is a top view of yet another template for use in providing a bolus injection to a patient through the multiple reservoir pump of FIG. 7.

The template system for use in conjunction with pump 10' preferably includes template 100' for use in refilling chamber 16', template 200' for use in refilling chamber 14', and template 300' for use in providing a direct injection to a patient through bolus port 46'. Clearly, these templates correspond to above described templates 100, 200 and 300 with like elements being denoted by the addition of a prime ("'"). Each of the templates preferably includes a contoured or concave seating surface or the like for cooperating with a convex surface A' or the like of the top surface of pump 10', and a recessed seating surface or the like for cooperating with an extending surface B' or the like of the top surface of pump 10'. In a preferred embodiment, template 100' includes an opening 104' for guiding a needle or syringe to refill chamber 16', template 200' includes an opening 204' for use in refilling chamber 14', and template 300' includes an opening 304' for use in providing a direct injection to a patient via bolus port 46'. Once again, depending upon the desired chamber to refill, a doctor or other medical professional chooses either template 100' or 200'. And, should a direct injection be desired, template 300' is chosen. Thus, templates 100', 200' and 300' are substantially similar to templates 100, 200 and 300, but configured to cooperate with pump 10'. While extending surface B' is shown in FIG. 7b to be raised septum 26', it is noted that any of septa 26', 32' or 48' may be raised to be an extending surface B'. In addition, it is noted that more than one of these surfaces may be raised, to cooperate with more than one recessed seating surface of any of templates 100', 200' or 300'.

Figure 11:
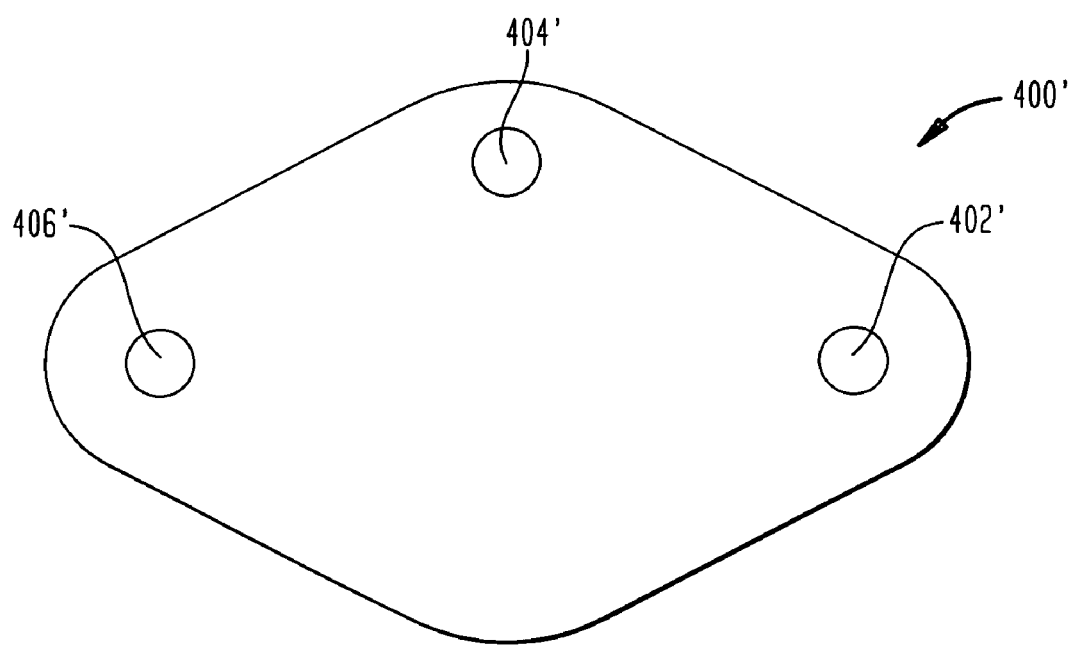
FIG. 11 is a top view of a template for use in refilling two reservoirs of the multiple reservoir pump of FIG. 7, and for use in providing a bolus injection to a patient through the same pump.

As with the above described single template 400, which cooperates with pump 10, it is contemplated to provide a singe template 400' for cooperating with pump 10'. As shown in FIG. 11, template 400' includes three openings. Preferably, opening 402' is for use in refilling chamber 16', opening 404' is for use in refilling chamber 18', and opening 406' is for use in providing a direct injection to a patient through bolus port 46'. As in all of the previous examples, template 400' preferably includes a contoured or concave seating surface for cooperating with a convex portion A' of the top surface of pump 10', and a recessed seating surface for cooperating with an extending portion B' of the top surface of pump 10'. In addition, it is contemplated to provide template 400' with indicia which identify the individual openings and the ports that they correspond to.

Figure 12:
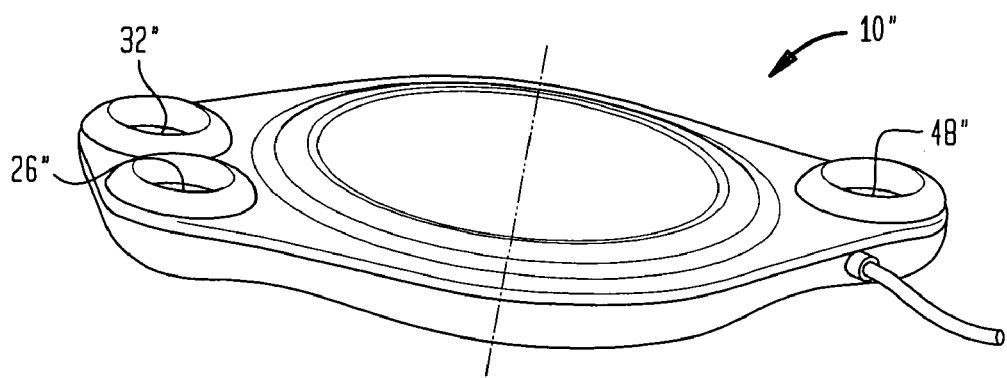
FIG. 12 is a perspective view of another embodiment multiple reservoir implantable pump.
Figure 13:
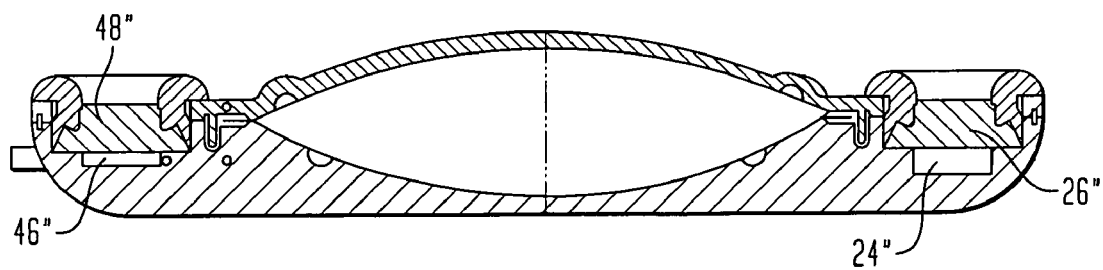
FIG. 13 is a cross sectional front view of the implantable pump shown in FIG. 12.
Figure 14:
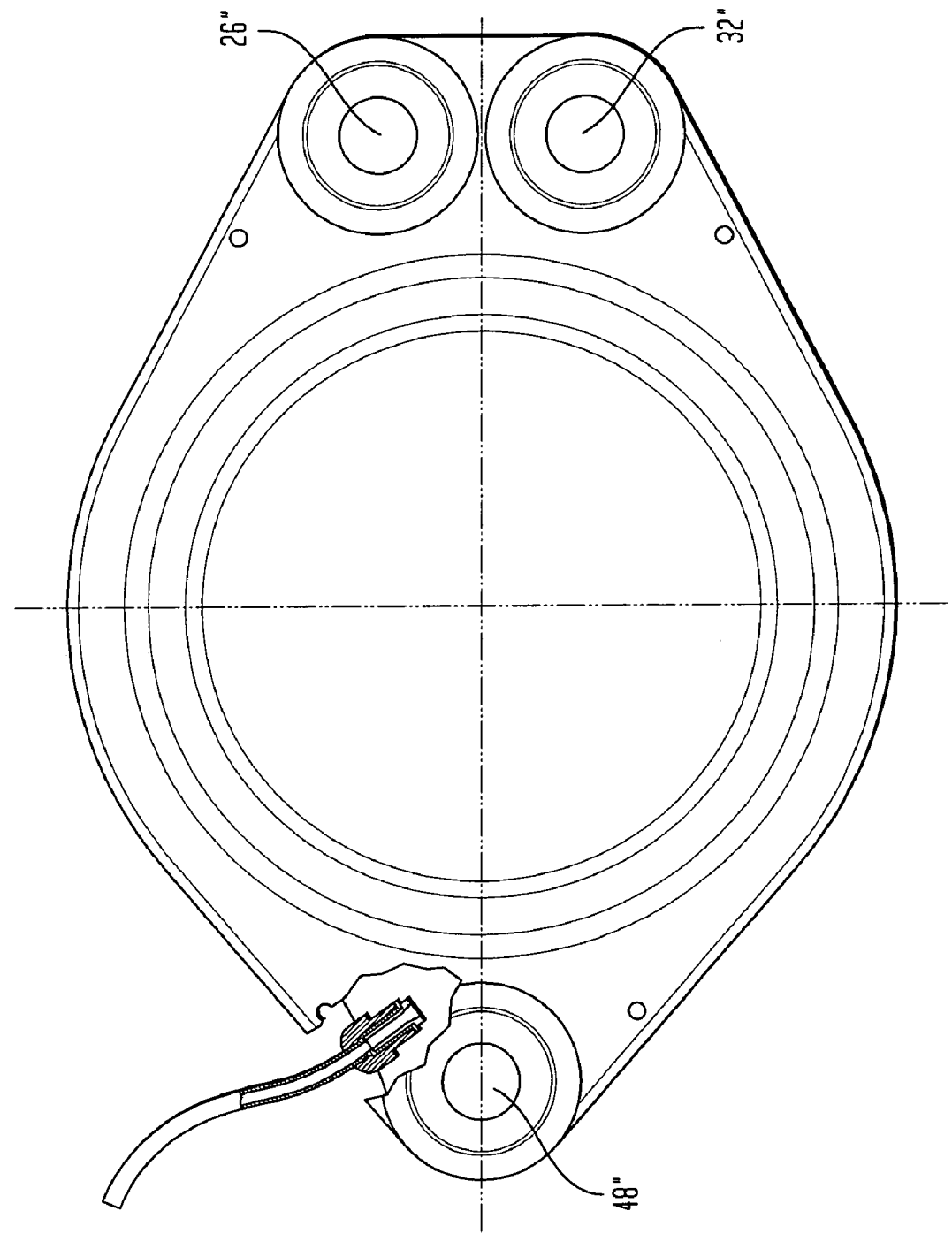
FIG. 14 is a top view of the implantable pump shown in FIG. 12.
Figure 15:
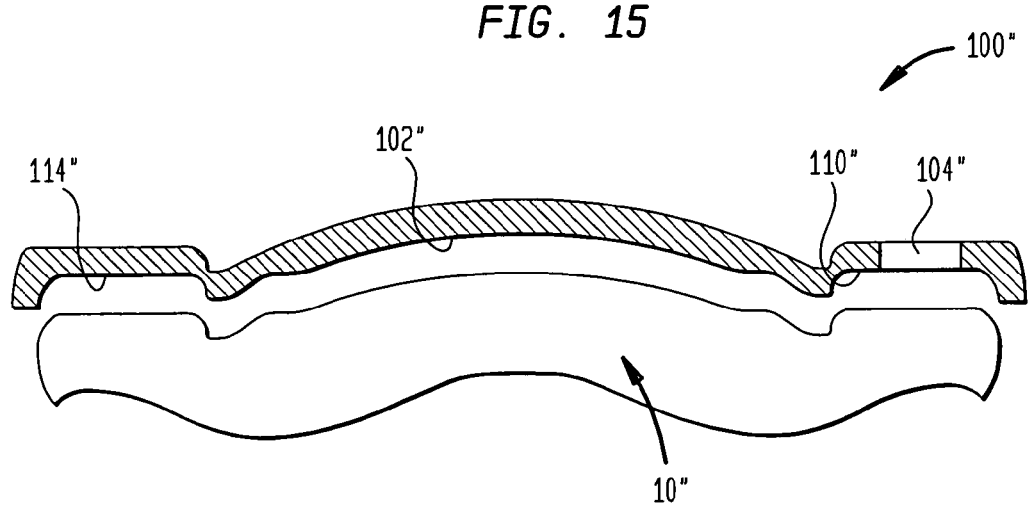
FIG. 15 is a cross sectional side view of template for use in filling one reservoir of the multiple reservoir shown in FIGS. 12-14.

Yet another preferred embodiment implantable pump and corresponding template system is depicted in FIGS. 12-16. FIGS. 12-14 depict a differently configured pump 10", than that of the above described pumps 10 and 10'. However, pump 10" does include certain like elements to those pumps, which are identified with like reference numerals and a double prime ("''") identifier. Essentially, pump 10" is identical to pumps 10 and 10', but with its various septum (and underlying ports) being situated in yet another configuration. As shown in FIGS. 12 and 14, rather than having a septum 32 surrounding a septum 26 (as in pump 10), or a septum 32' displaced from a septum 26' (as in pump 10'), pump 10" includes septums 26" and 32", which are adjacent one another with their underlying ports 24" and 30" (not shown) connected through appropriate passageways 28" and 34" (not shown) to chambers 14" and 16" respectively. In addition, septa 26", 32"and 48"are each raised septa thereby forming projections extending from pump 10". Nonetheless, the operation of pump 10" is substantially similar to that described above.

Figure 16:
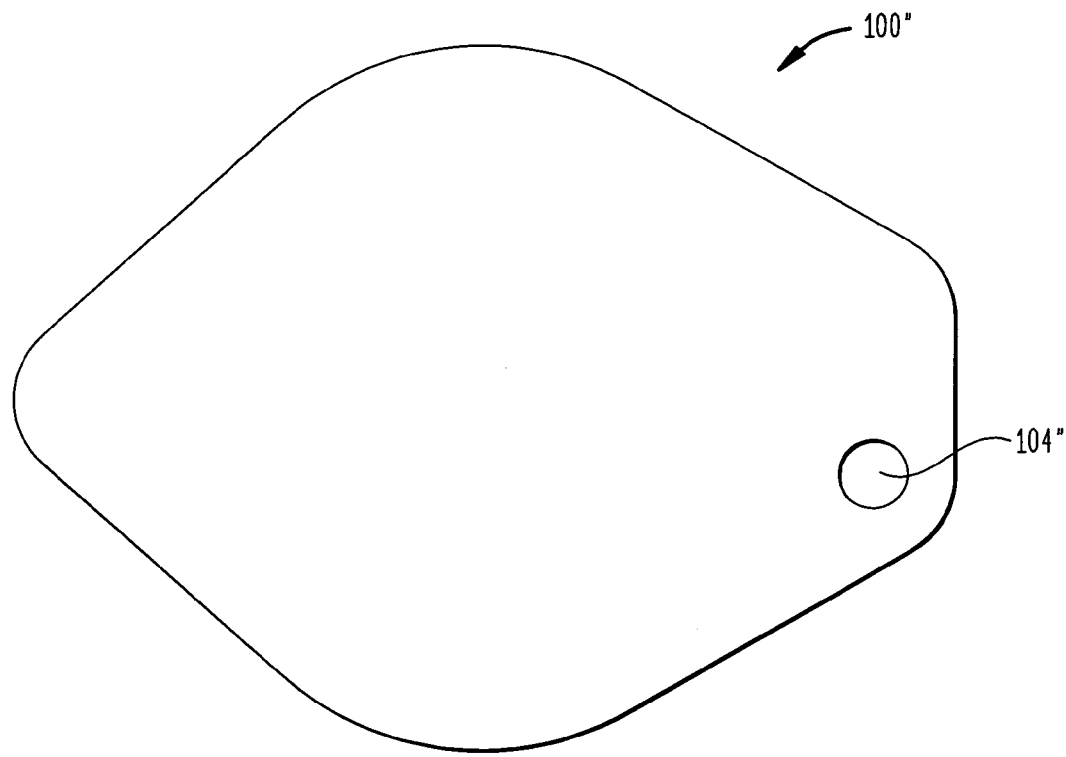
FIG. 16 is a top view of the template shown in FIG. 15.

The template system for use in conjunction with pump 10" preferably includes anywhere from one to three templates. Most preferably, the template system includes a template 100" (shown in FIGS. 15 and 16) for use in refilling chamber 16", a template 200" (not shown) for use in refilling chamber 14", and a template 300" (not shown) for use in providing a direct injection to a patient thorough bolus port 46". Once again, these templates correspond to the above described templates for use with pumps 10 and 10', with like elements being denoted by the addition of a double prime ("''") indicator. Essentially, the three templates are structurally similar to the above described templates of the other embodiments, with each template including a differently positioned opening for allowing a needle/syringe to inject into a different port. For example, as shown in FIG. 16, template 100" includes an opening 104" for use in filling port 24". However, in the template system of this embodiment, each of templates 100", 200" and 300" includes surfaces for cooperating with the aforementioned raised septa. Each of the templates preferably includes a concave seating surface or the like for cooperating with a convex surface A" or the like of the top surface of pump 10". In addition, each of the templates preferably includes three seating surfaces for cooperating with septa 26", 32" and 48" of pump 10". For example, as shown in the Figures, template 100" includes a concave surface 102" for cooperating with convex surface A" of pump 10", and seating surfaces 110", 112" (only 110" of which is visible in FIG. 15) and 114" for cooperating with septa 26", 32" and 48", respectively. It is noted that templates 200" and 300" are similarly configured. This type of design ensures that the particular template being utilized is positioned correctly over pump 10". Finally, it is noted that a single template (not shown) with three openings corresponding to the various ports of pump 10" may be provided. This is similar to the above described templates 400 and 400'.

Those of ordinary skill in the art will clearly recognize from the foregoing description that many different templates may be provided that correspond to different implantable pumps. Depending upon the size and/or shape of the particular implantable pump, corresponding templates may easily be provided. Whatever the particular pump design, like templates are capable of being provided. For example, pumps including fewer than or more ports may have corresponding templates which include like number of openings and/or different templates for use in filling/injecting fluid into the particular ports. In addition, whether a single template or multiple templates are provided in the template system, the use of the template(s) should be evident from the present disclosure. Nevertheless, templates in accordance with the present invention preferably include at least two seating surfaces or other alignment aids for providing at least two reference points for cooperation with corresponding portions of an implantable pump to assure proper seating and alignment of the openings of the template with the proper septum. As is clearly understood by those of ordinary skill in the art, such a design ensures proper alignment of the template with respect to the corresponding implantable pump.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of refilling an implantable infusion pump implanted in a patient, said method comprising the steps of:
   providing a first template including first means for aligning with pump alignment means of said pump to ensure alignment of said first template with respect to said pump and a second template including second means for aligning with the pump alignment means to ensure alignment of said second template with respect to said pump, said first and second templates being separate from each other;
   placing said first template over a section of skin of the patient adjacent said pump, so as to align said first means for aligning with said pump alignment means;
   injecting a needle through an opening formed in said first template, through the skin of the patient, and into a first port corresponding to a first chamber of said pump;
   placing said second template over a section of skin of the patient adjacent said pump, so as to align said second means for aligning with said pump alignment means; and
   injecting a needle through an opening formed in said second template, through the skin of the patient, and into a second port corresponding to a second chamber of said pump.

2. The method according to claim 1, further comprising the steps of:

providing a third template including third means for aligning with pump alignment means of said pump to ensure alignment of said third template with respect to said pump, said third template being separate from said first and second templates;

placing said third template over a section of skin of the patient adjacent said pump, so as to align said third means for aligning with said pump alignment means.

3. The method according to claim 2, further comprising the step of injecting a needle through an opening formed in said third template, through the skin of the patient, and into a third port of said pump, the third port allowing for direct injection into the patient.

4. The method according to claim 1, wherein said first and second means for aligning include two recessed surfaces and said pump alignment means include two raised portions, the recessed surfaces being capable of cooperating with the raised portions.

5. The method according to claim 1, wherein said first and second means for aligninq include two protrusions and said pump alignment means include two depressions, the protrusions being capable of cooperating with the depressions.

6. The method according to claim 1, wherein said first and second means for aligning include at least one recessed surface and at least one protrusion and said pump alignment means include at least one raised portion and at least one depression, the recessed surface being capable of cooperating with the raised portion and the protrusion being capable of cooperating with the depression.

7. A method of refilling an implantable infusion pump implanted in a patient, said method comprising the steps of:

placing a first template having a first opening, a first template structure, and a second template structure over a section of skin of the patient adjacent the pump, so as to align the first template structure with a first pump structure of the pump and to align the second template structure with a second pump structure of the pump, wherein the aligned template and pump structures ensure proper alignment of the first template with respect to the pump;

injecting a needle through the opening of the first template, and into a first port corresponding to a first chamber of the pump; and placing a second template having a second opening, a third template structure, and a fourth template structure over a section of skin of the patient adjacent the pump, so as to align the third template structure with the first pump structure and to align the fourth template structure with the second pump structure, wherein the second template is separate from the first template and the aligned template and pump structures ensure proper alignment of the second template with respect to the pump;

injecting a needle through the second opening of the second template, and into a second port corresponding to a second chamber said pump, wherein the template structures are either recessed surfaces or raised portions and the corresponding pump structures are the other of recessed surfaces or raised portions.

8. The method according to claim 7, further comprising the step of placing a third template having a third opening, a fifth template structure, and sixth template structure over a section of skin of the patient adjacent the pump, so as to align the fifth template structure with the first pump structure and to align the sixth template structure with the second pump structure, wherein third template is separate from the first and second templates and the aligned template and pump structures ensure proper alignment of the third template with respect to the pump.

9. The method according to claim 8, further comprising the step of injecting a needle through the third opening of the third template, and into a third, port of the pump, the third port allowing for direct injection into the patient.

10. The method according to claim 7, wherein the first template structure is a recessed surface and the first pump structure is a raised portion and the second template structure is a recessed surface and the second pump structure is a raised portion.

11. The method according to claim 10, wherein the third template structure is a recessed surface and the first pump structure is a raised portion and the fourth template structure is a recessed surface and the second pump structure is a raised portion.

12. The method according to claim 11, wherein the fifth template structure is a recessed surface and the first pump structure is a raised portion and the sixth template structure is a recessed surface and the second pump structure is a raised portion.

13. A method of refilling an implantable infusion pump implanted in a patient, said method comprising the steps of:

placing a first template having a first opening, a first template recessed surface, and a second template recessed surface over a section of skin of the patient adjacent the pump, so as to align the first template recessed surface with a first pump raised portion of the pump and to align the second template recessed surface with a second pump raised portion of the pump, wherein the aligned template recessed surfaces and pump raised portions ensure proper alignment of the first template with respect to the pump;

injecting a needle through the opening of the first template, and into a first port corresponding to a first chamber of the pump;

placing a second template having a second opening, a third template recessed surface, and a fourth template recessed surface over a section of skin of the patient adjacent the pump, so as to align the third template recessed surface with the first pump raised portion and to align the fourth template recessed surface with the second pump raised portion, wherein the second template is separate from the first template and the aligned template recessed surfaces and pump raised portions ensure proper alignment of the second template with respect to the pump;

injecting a needle through the second opening of the second template, and into a second port corresponding to a second chamber of said pump;

placing a third template having a third opening, a fifth template recessed surface, and sixth template recessed surface over a section of skin of the patient adjacent the pump, so as to align the fifth template recessed surface with the first pump raised portion and to align the sixth template recessed surface with the second pump raised portion wherein the third template is separate from the first and second templates and the aligned template recessed surfaces and pump raised portion ensure proper alignment of the third template with respect to the pump; and injecting a needle through the third opening of the third template, and into a third port of the pump, the third port allowing for direct injection into the patient.

* * * * *

UNITED STATES PATENT AND TRADEMARK OFFICE
CERTIFICATE OF CORRECTION

PATENT NO.         : 7,708,730 B2                               Page 1 of 1
APPLICATION NO.    : 11/342391
DATED              : May 4, 2010
INVENTOR(S)        : Bernd Steinbach and Sidney David It is certified that error appears in the above-identified patent and that said Letters Patent is hereby corrected as shown below:

Title page, under Item (57) Abstract, line 6, "cooperating with a" should read --cooperating with--.
Column 1, line 31, "include a housing" should read --includes a housing--.
Column 2, line 28, "includes at least" should read --include at least--.
Column 3, line 22, "another templates" should read --another template--.
Column 6, line 42, "templates are useful" should read --templates is useful--.
Column 8, line 35, "system is depicted" should read --system are depicted--.
Column 9, line 24, "system is depicted" should read --system are depicted--.
Column 11, line 20, "aligninq" should read --aligning--.
Column 11, line 55, Claim 7, "chamber said pump" should read --chamber of said pump--.
Column 11, line 67, Claim 7, "wherein third" should read --wherein the third--.

Signed and Sealed this
Eighteenth Day of September, 2012

David J. Kappos
*Director of the United States Patent and Trademark Office*